US00PP11286P

United States Patent [19]

Falstad, III

[11] Patent Number: Plant 11,286

[45] Date of Patent: Mar. 14, 2000

[54] HOSTA PLANT NAMED 'ARISTOCRAT'

[76] Inventor: Clarence H. Falstad, III, 152 Birchwood, Holland, Mich. 49423-6657

[21] Appl. No.: 09/076,084

[22] Filed: May 11, 1998

[51] Int. Cl.[7] ..... A01H 5/00

[52] U.S. Cl. ..... Plt./353

[58] Field of Search ..... Plt./353

[56] References Cited

U.S. PATENT DOCUMENTS

P.P. 2,467 1/1965 Grullemans ..... Plt./353

P.P. 8,016 10/1992 Falstad, III ..... Plt./353

*Primary Examiner*—Howard J. Locker

*Assistant Examiner*—Wendy Anne Baker

[57] ABSTRACT

The unique new mutation of Hosta 'Hadspen Blue' characterized by a wide jagged margin of creamy-yellow to creamy-white on a blue-green leaf named Hosta 'Aristocrat'.

4 Drawing Sheets

SUMMARY, BACKGROUND, AND ORIGIN OF INVENTION

The new variety of Hosta is a tissue culture derived sport of the cultivar Hosta 'Hadspen Blue', named Hosta 'Aristocrat', and hereinafter also called "the plant." I discovered the plant as a mutation of a stock plant of 'Hadspen Blue' growing in a tissue culture propagation laboratory at a nursery in Zeeland, Mich. USA. The mutation was not intentionally induced, and no mutagen was used. The initial sport, found in June of 1992, was of a sectorial chimera nature. In April of 1993 one of these plants had stabilized to produce a periclinal chimera variegation with a cream margin.

Hosta 'Hadspen Blue' is a hybrid of the late Eric Smith of Southampton, England. It is a cross between Hosta 'Tardiflora'(unpatented)×*Hosta sieboldiana,* and was originally given the cross number of "2×7", known for its very blue leaf color. Although other hybrids of Eric Smith's have produced variegated sports, this is the only one from the stock of Hosta 'Hadspen Blue' (unpatented). Such sports include Hosta 'June' (unpatented) and Hosta 'Sleeping Beauty' (unpatented), both from 'Halcyon' (unpatented); also 'Blueberries and Cream' (unpatented) from 'Dorset Blue' (unpatented).

I have asexually propagated the plant successfully by both tissue culture and division of the rhizome and produced plants with the same characteristics of the original plant. Following the tissue culture procedures developed and improved by me at a nursery in Zeeland, Mich., the plant has been successfully asexually reproduced.

DETAILED DESCRIPTION OF THE INVENTION

Figure 1:
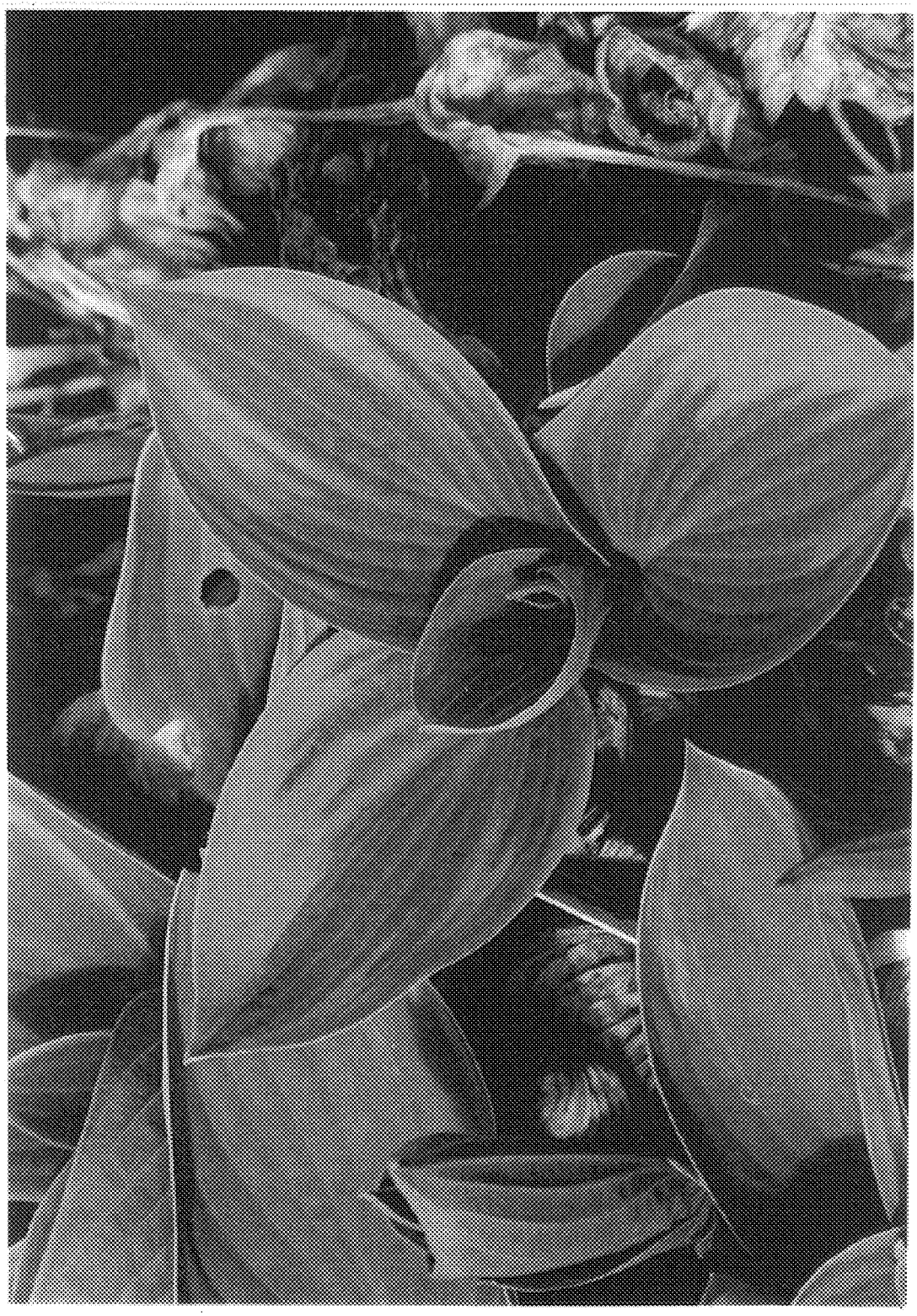
FIG. 1 shows the plant in early spring at a very young stage with the yellow-green colored margins.
Figure 2:
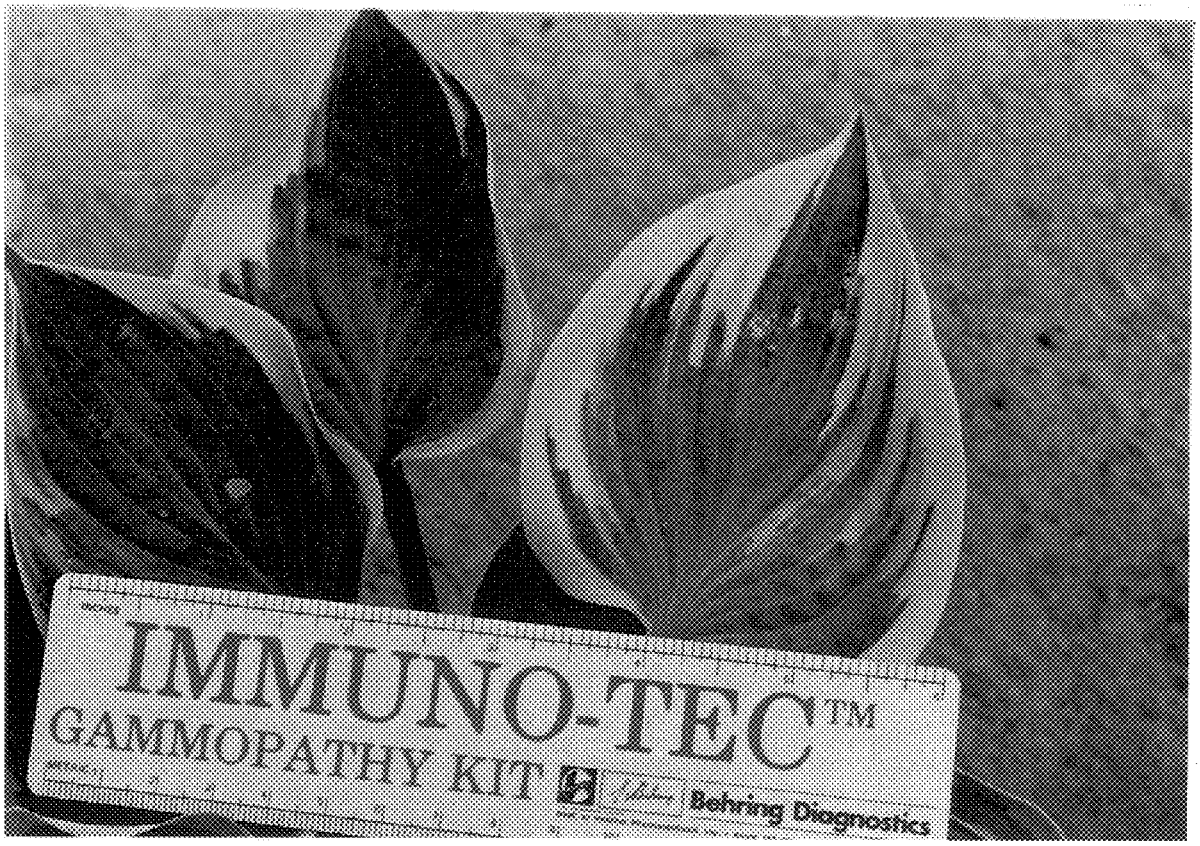
FIG. 2 shows a close up of three single leaves with the margin, inside and intermediate colors.
Figure 3:
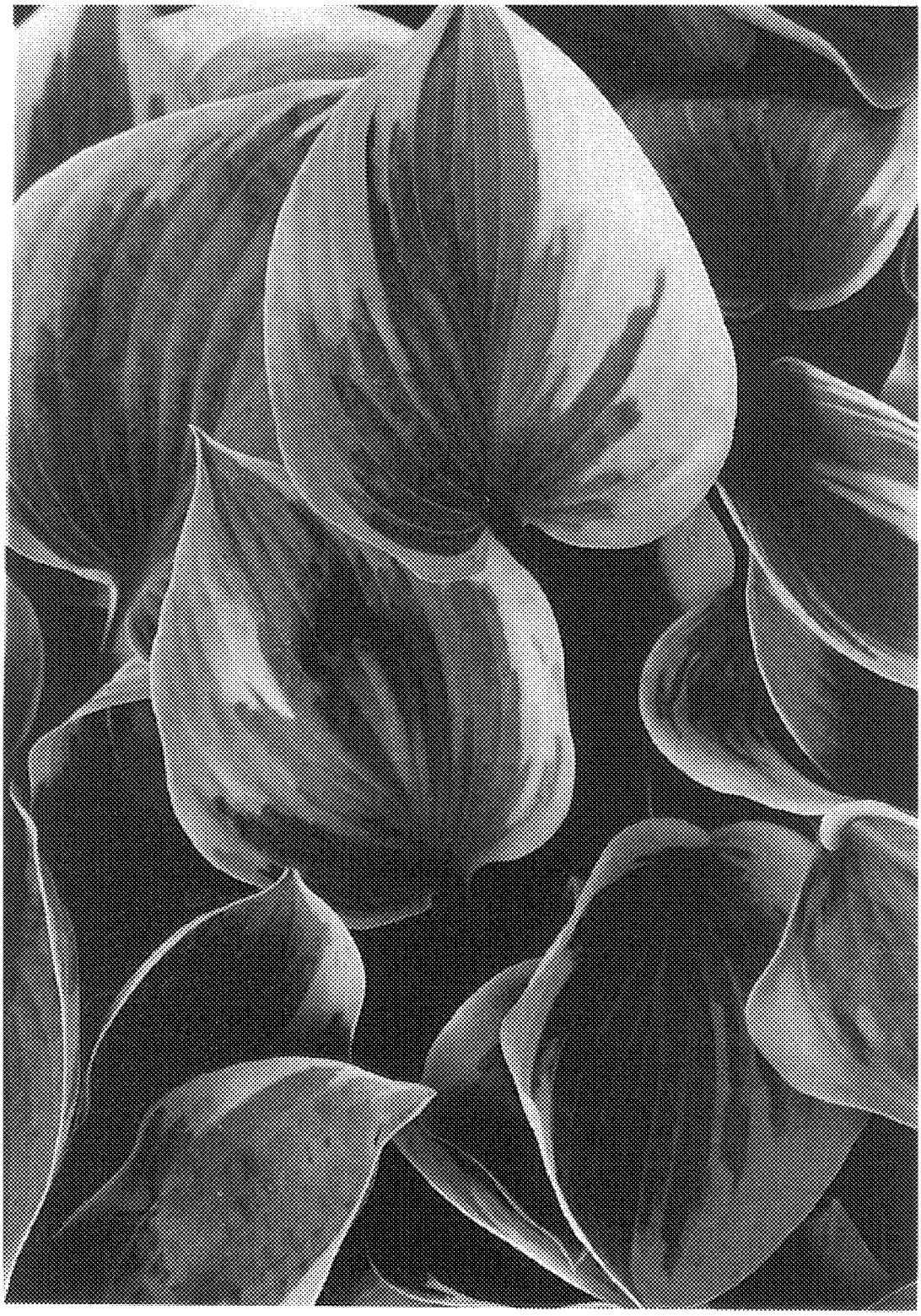
FIG. 3 shows a close-up of several leaves of the plant.
Figure 4:
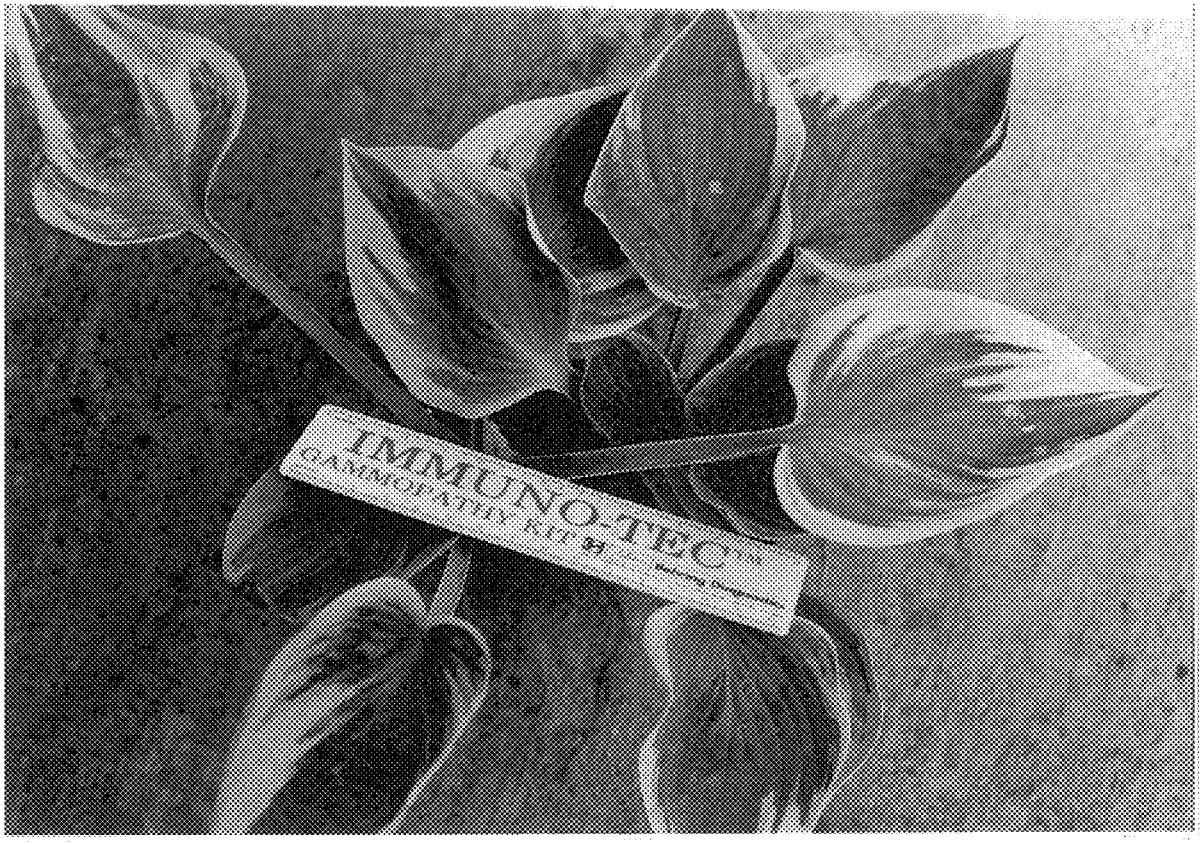
FIG. 4 shows the plant at an early summer stage and the difference in margin color between new leaves just emerging and leaves that have been open longer.

Hosta 'Hadspen Blue' is a densely rhizomatous herbaceous perennial with short subterranean stems and petioled, tufted leaves. The leaves are nearly round with a sharply pointed apex and auriculate leaf base. Hosta 'Hadspen Blue' has a very glaucous surface producing a blue effect. The leaves produce a clump reaching 16 to 18 inches in height (40.6 to 45.7 cm) and 24 to 36 inches in width (61 to 91.4 cm). Each leaf blade measures 6.5 to 7.5 inches long (16.5 to 19 cm) by 5.5 to 6.5 inches wide (14 to 19 cm) at maturity. Plants may take five to seven years to reach full mature characteristics. In this time the leaves become larger, more rounded, and seersuckered or dimpled. The number of leaf vein pairs increases to a maximum of 12 on either side of the mid-rib.

Flowers are a light lavender with a clear rim. They are held very tightly together on scapes 18 to 20 inches (45.7 to 50.8 cm) tall. Each flower is about 1.75 to 2 inches (4.4 to 5.1 cm) long and about 1.5 inches (3.8 cm) wide. In west Michigan the flowers usually appear about the third week of July and last for about three weeks.

The new variety, Hosta 'Aristocrat', is unique from Hosta 'Hadspen Blue' in that it has a wide variegated margin. All color references are given according to The Royal Horticultural Society Colour Chart. The margin starts off in the early spring as a Yello-Green 144 B using The Royal Horticultural Society Colour Chart, and progressively lightens to a Yellow 10 A to 9 C and finally a 10 D or lighter depending on how much light and/or heat the plant gets as it grows. The center starts out about a Green 141 B and becomes more blue to a 122 A or bluer. There are also some different colors between the margin and center portion of the leaf. These are formed from the uneven folding of the outer histogenic layer (L 1) over the inner layer (L 2) producing some intermediate colors of Blue-Green 122 C and near a Green 151 B. The wax can be washed off revealing a Green 137 A. The underside of the leaf is also glaucous producing a lighter blue in the area of Blue-Green 122 C. These colors may vary depending on environmental and growing conditions. Normally, hostas are grown with some shade. If the plant is grown in more sun to nearly full sun, the leaf colors will change more rapidly in the spring and may bleach out to a very light yellow green in the center and near white to white margin. The plant typically has petioles measuring 10 to 14 inches (25 to 35 cm) long. This varies with location in a clump, maturity, plant health shade intensities and night and day temperatures and the differences between day and night.

The flowers of Hosta 'Aristocrat' are essentially like those of Hosta 'Hadspen Blue'. Each division has at most one scape measuring 18 to 20 inches (45.7 to 50.8 cm) tall, and may have as many as 24 to 36 funnel-form flowers depending on health of the plant. There are six tepals arranged in two sets of three. The individual tepals are sharply eliptical, 5/16 to 3/8 inch wide and 1½ to 1⅞ long and fused at about their mid-point. Tepal color is near a group 85 D and 84C violet in the middle one third of the tepal surrounded by a white portion with a thin one to two millimeters clear ring. The calyx is 1.75 to 2 inches (4.4 to 5.1 cm) long and about 1.5 inches (3.8 cm) wide. There is no notable fragrance of the flower. A day before anthesis the bud is about 1¼ to 1½ inches (3.0 to 3.5 cm) long and about ½ inch (1.0 cm) in diameter. Each flower is subtended by a single bract 1 to 1¼ inches (2.5 to 3.0 cm) long by ½ inch (1.0 cm) wide, in the green group about 137D to 139B and held on a pedicle. Each flower has six stamens held on filaments slightly shorter than the tepals and style and curved to nearly 90 degrees at the distal end. Fruit is a three carpeled capsule about 1 inch (2.5 cm) long depending on fertilization. There are about six to 15 single-winged black seed per carpel. The light lavender flower is near a Violet group 85 D and 84 C (using The Royal Horticultural Colour Chart). Like the leaf color, the flowers may vary in intensity based on the growing conditions, fertilizer, and environmental conditions. For example, plants grown in areas with more intense heat or less sun tend to produce plants with less pigment.

Hosta 'Aristocrat' is like Hosta 'Hadspen Blue' in all other ways, similar leaf size and shape, identical clump size and shape, and the same hardiness and disease tolerance. The plant is hardy to at least zone 3 on the USDA hardiness chart, and is slightly susceptible to some slugs and snails as are most hostas. The plant does not appear to have any altered ploidy state and would contain the normal diploid chromosome number of 60n for hostas.

I claim:

1. The new and unique variety of Hosta plant named 'Aristocrat' with a blue-green leaf and cream-colored margin substantially as described and illustrated.

* * * * *